(12) United States Patent
Guan et al.

(10) Patent No.: US 10,039,489 B2
(45) Date of Patent: Aug. 7, 2018

(54) PERIODONTAL DISEASE DETECTION SYSTEM AND METHOD

(71) Applicant: Carestream Dental Technology Topco Limited, London (GB)

(72) Inventors: Yiyi Guan, Pittsford, NY (US); Victor Wong, Pittsford, NY (US)

(73) Assignee: Carestream Dental Technology Topco Limited, London (GB)

(*) Notice: Subject to any disclaimer, the term of this patent is extended or adjusted under 35 U.S.C. 154(b) by 0 days.

(21) Appl. No.: 15/029,661

(22) PCT Filed: Nov. 5, 2014

(86) PCT No.: PCT/US2014/064037
§ 371 (c)(1),
(2) Date: Apr. 15, 2016

(87) PCT Pub. No.: WO2015/069704
PCT Pub. Date: May 14, 2015

(65) Prior Publication Data
US 2016/0270716 A1    Sep. 22, 2016

Related U.S. Application Data

(60) Provisional application No. 61/900,560, filed on Nov. 6, 2013.

(51) Int. Cl.
*G06K 9/00* (2006.01)
*A61B 5/00* (2006.01)
(Continued)

(52) U.S. Cl.
CPC ........ *A61B 5/4552* (2013.01); *A61B 1/00009* (2013.01); *A61B 1/00066* (2013.01); (Continued)

(58) Field of Classification Search
None
See application file for complete search history.

(56) References Cited

U.S. PATENT DOCUMENTS 5,149,503 A * 9/1992 Kohno ................ A61B 5/0059 356/39
5,284,137 A * 2/1994 Kessler ................ G01N 21/314 128/898

(Continued)

OTHER PUBLICATIONS

International Search, International application No. PCT/US2014/064037, dated Apr. 8, 2015, 3 pages.
(Continued)

*Primary Examiner* — Vu Le
*Assistant Examiner* — Samah Beg (57) ABSTRACT

Intra-oral imaging apparatus and/or method embodiments can provide digital dental reflectance images used to identify selected areas of interest (AOI) within a dental region of interest (ROI) having selected image characteristics for both hemoglobin's total concentration and oxygenation level. In one embodiment, reflectance images can determine relative total hemoglobin using at least a wavelength band that includes an isobestic wavelength for absorption coefficients of oxyhemoglobin ($HbO_2$) and deoxyhemoglobin (Hb). In one embodiment, intra-oral imaging apparatus and/or method embodiments can use reflectance images of a dental region at least at three wavelengths; a control logic processor for processing the reflectance images to determine relative tHb and its relative oxygenation level and/or identify disease areas having periodontal tissues condition; and a display for displaying periodontal tissues or a visual indication of the areas having selected imaging characteristic determined by the reflectance images.

16 Claims, 7 Drawing Sheets

(51) Int. Cl.
*A61B 1/00* (2006.01)
*A61B 1/04* (2006.01)
*A61B 1/06* (2006.01)
*A61B 1/24* (2006.01)
*A61B 5/1459* (2006.01)

(52) U.S. Cl.
CPC .............. *A61B 1/04* (2013.01); *A61B 1/0684* (2013.01); *A61B 1/24* (2013.01); *A61B 5/0088* (2013.01); *A61B 5/1459* (2013.01); *A61B 5/7264* (2013.01); *A61B 5/7282* (2013.01)

(56) References Cited

U.S. PATENT DOCUMENTS

| | | | | |
|---|---|---|---|---|
| 5,413,100 | A * | 5/1995 | Barthelemy | A61B 5/14551 600/326 |
| 5,692,503 | A * | 12/1997 | Kuenstner | A61B 5/14551 356/41 |
| 7,596,253 | B2 * | 9/2009 | Wong | H04N 17/002 382/128 |
| 8,073,212 | B2 * | 12/2011 | Gerlach | A61B 5/0088 382/128 |
| 2003/0236647 | A1 * | 12/2003 | Yoon | A61B 5/02007 702/183 |
| 2004/0204651 | A1 * | 10/2004 | Freeman | A61B 5/0075 600/473 |
| 2010/0280392 | A1 * | 11/2010 | Liu | A61B 5/7264 600/475 |
| 2012/0130208 | A1 * | 5/2012 | Kuhn | A61B 5/1459 600/310 |
| 2012/0184831 | A1 * | 7/2012 | Seetamraju | A61B 5/0075 600/324 |
| 2013/0096403 | A1 * | 4/2013 | Dacso | A61B 5/14551 600/324 |
| 2013/0172741 | A1 * | 7/2013 | Kusukame | A61B 5/0075 600/438 |
| 2013/0204102 | A1 * | 8/2013 | Sen | A61B 5/14535 600/322 |
| 2014/0073891 | A1 * | 3/2014 | Stoddart | A61B 5/4845 600/328 |
| 2016/0015493 | A1 * | 1/2016 | Ertl | A61B 6/145 433/215 |
| 2016/0038033 | A1 * | 2/2016 | Lal | A61B 5/0088 433/29 |
| 2016/0125601 | A1 * | 5/2016 | Wu | G06T 7/0012 382/128 |
| 2016/0287063 | A1 * | 10/2016 | Ramanujam | A61B 1/00082 |

OTHER PUBLICATIONS

Kan-Zhi Liu et al., In vivo determination of multiple indices of periodontal inflammation by optical spectroscopy, Journal of Periodontal Research, doi:10.1111/j.1600-0765.2008.01112.x, 2009; vol. 44, pp. 117-124, 2009.

T. Hanioka et al., Haemoglobin Concentration and Oxygen Saturation in Dog Gingiva With Experimentally Induced Periodontitis, Archs oral Biol., vol. 34, No. 8, pp. 657-663, 1989.

T. Hanioka et al., Hemoglobin concentration and oxygen saturation of clinically healthy and inflamed gingival in human subjects, Journal of Periodontal Research, 1990, vol. 25, pp. 93-98.

C. Zakian et al., In vivo quantification of gingival inflammation using spectral imaging, Journal of Biomedical Optics, vol. 13(5), 054045, Sep./Oct. 2008), pp. 1-10.

C.S. Prasanth et al., Non-invasive detection of periodontal disease using diffuse reflectance spectroscopy: a clinical study, Proceedings of SPIE, vol. 8230, 2012, pp. 1-11, XP055180879.

P.C. Sekhar et al., Discrimination of periodontal diseases using diffuse reflectance spectral intensity ratios, Journal of Biomedical Optics, 2012, vol. 17, No. 2, pp. 1-10, XP055180954, ISSN: 1560-2281.

Zili Ge et al., Assessment of Local Hemodynamics in Periodontal Inflammation Using Optical Spectroscopy, Journal of Periodontol, 2011, vol. 82, pp. 1161-1168.

Chandra Sekhar Prasanth et al., In vivo inflammation mapping of periodontal disease based on diffuse reflectance spectral imaging: a clinical study, Journal of Biomedical Optics, vol. 18(2), Feb. 2013, pp. 1-9.

* cited by examiner

PERIODONTAL DISEASE DETECTION SYSTEM AND METHOD

CROSS REFERENCE TO RELATED APPLICATIONS

This application claims the benefit of and is a U.S. National Phase filing of PCT Application PCT/US14/064037 filed Nov. 5, 2014 entitled "PERIODONTAL DISEASE DETECTION SYSTEM AND METHOD", in the name of Guan et al, which claims the benefit of U.S. Provisional application U.S. Ser. No. 61/900,560, provisionally filed on Nov. 6, 2013, entitled "PERIODONTAL DISEASE DETECTION SYSTEM AND METHOD", in the names of Guan et al, all of which are incorporated herein in their entirety.

FIELD OF THE INVENTION

This invention generally relates to methods and apparatus for dental imaging and more particularly relates to apparatus and methods for identifying and highlighting conditions in still and/or video images that are obtained from a patient's teeth.

BACKGROUND OF THE INVENTION

Periodontal disease is a disease of tissues surrounding the teeth and a cause of edentulism. It starts with a reversible gingival inflammation (Gingivitis) and grows towards an inflammation with the loss of tissue attachment and bone tissue (Periodontitis). A technique of detection is desirable for the prevention and control of this disease. Traditional diagnosis methods are viewed by some as being subjective and invasive, and can cause considerable patient discomfort.

SUMMARY

An aspect of this application is to advance the art of medical digital imaging.

Another aspect of this application is to address, in whole or in part, at least the foregoing and other deficiencies in the related art.

It is another aspect of this application to provide, in whole or in part, at least the advantages described herein.

It is an object of the present invention to advance the art of dental imaging for intra-oral assessment.

An advantage offered by apparatus and method embodiments of the present application relates to improved imaging of soft tissue that enables an intra-oral camera with video mode and/or still image mode to be used to detect or assess periodontal diseases. Another advantage offered by apparatus and method embodiments of the present application relates to improved imaging of soft tissue that enables an intra-oral camera to provide accurate and repeatable periodontal diseases measurements achieved by multi-wavelength imaging and calculations. Another advantage offered by apparatus and method embodiments of the present invention relates to calculating concentration of tHb and its oxygenation through diffuse reflectance intensities using at least three wavelengths. Another advantage offered by apparatus and method embodiments of the present application relates to improved imaging of dental soft tissue for periodontal analysis at lower cost over conventional methods.

These objects are given only by way of illustrative example, and such objects may be exemplary of one or more embodiments of the invention. Other desirable objectives and advantages inherently achieved by apparatus and method embodiments of the present application may occur or become apparent to those skilled in the art. The invention is defined by the appended claims.

According to one aspect of the disclosure, there is provided a method of capturing a digital dental image that can include illuminating a dental region of interest (ROI) using light sources; capturing reflectance images by receiving light reflected from ROI in narrow wavelength bands; processing captured reflectance images to determine relative tHb and its oxygenation level using at least a wavelength band that includes an isobestic wavelength for absorption coefficients of oxyhemoglobin ($HbO_2$) and deoxyhemoglobin (Hb); identifying selected areas of interest (AOI) within the dental ROI having selected pixel image characteristics of both hemoglobin's total concentration and oxygenation level; and displaying, storing, or transmitting the identified AOI within the dental ROI.

According to one aspect of the disclosure, there is provided an intra-oral imaging apparatus that can include an intraoral camera intraoral camera including an illumination module comprising light sources; an imaging sensor array receiving light reflected from tissue in narrow wavelength bands to capture reflectance images, where the reflectance images are captured at at least three wavelengths; a control logic processor for processing the captured reflectance images to determine relative tHb and its relative oxygenation level for identifying disease areas having periodontal tissues condition; and a display for displaying periodontal tissues or for displaying a color map of the identified disease areas having periodontal tissues condition.

According to one aspect of the disclosure, there is provided an intra-oral imaging apparatus that can include an intraoral camera including an illumination module comprising light sources; an imaging sensor array receiving light reflected from tissue in narrow wavelength bands to capture reflectance images, where the reflectance images are captured at least at three wavelengths; a control logic processor for processing the captured reflectance images to solve a set of equations using the intensities of the captured reflectance images at the at least three wavelengths to determine relative tHb and its relative oxygenation level for identifying disease areas having periodontal tissues condition; and a display for displaying periodontal tissues or for displaying a map of the identified disease areas having periodontal tissues condition.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DESCRIPTION OF EXEMPLARY EMBODIMENTS

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Ratios between two numbers are used in following description. It is understood that a ratio and its inverse provide equivalent information. Any use of ratios in this specification can be alternately constructed with the inverse.

This application describes exemplary non-invasive, optical imaging based system and/or method embodiments to detect periodontal disease. Applicants have noted an advantage in determining and monitoring the difference of hemoglobin (oxy- and deoxy-) concentration in combination with its oxygenation level in healthy and diseased periodontal tissues. Applicants have recognized that knowing both parameters of the hemoglobin's total concentration and oxygenation level can define periodontal tissue conditions more accurately.

The concentration of oxyhemoglobin ($HbO_2$) and deoxyhemoglobin (Hb) in tissues are correlated with inflammatory conditions of tissues. Some studies have indicated that the total concentration of $HbO_2$ and Hb increase at sites with gingivitis and periodontitis; and that the oxygenation level decreases with inflammatory conditions.

Figure 1A:
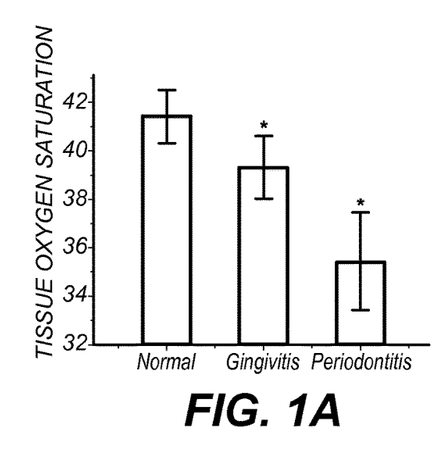
FIG. 1A is a diagram that illustrates that tissue oxygen saturation level decreases at sites with gingivitis and periodontitis relative to normal tissue.
Figure 1B:
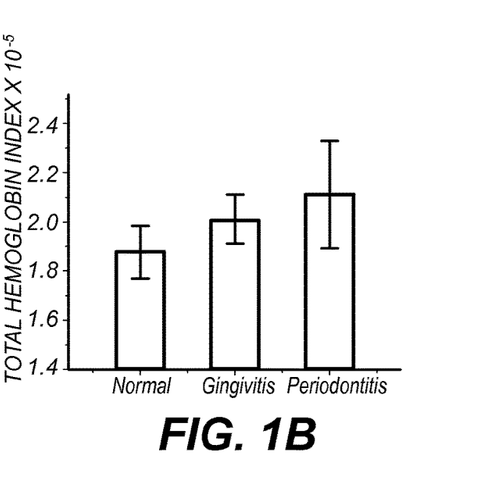
FIG. 1B is a diagram that illustrates that total hemoglobin index increases at sites with gingivitis and periodontitis relative to normal tissue.

One study has indicated that the concentration of total hemoglobin (tHb) increases with diseased periodontal tissue conditions; and the oxygenation level decreases with diseased periodontal tissues conditions. FIG. 1A is a diagram that illustrates that tissue oxygen saturation level decreases at sites with gingivitis and periodontitis relative to normal tissue. FIG. 1B is a diagram that illustrates that total hemoglobin index increases at sites with gingivitis and periodontitis relative to normal tissue.

Figure 2:
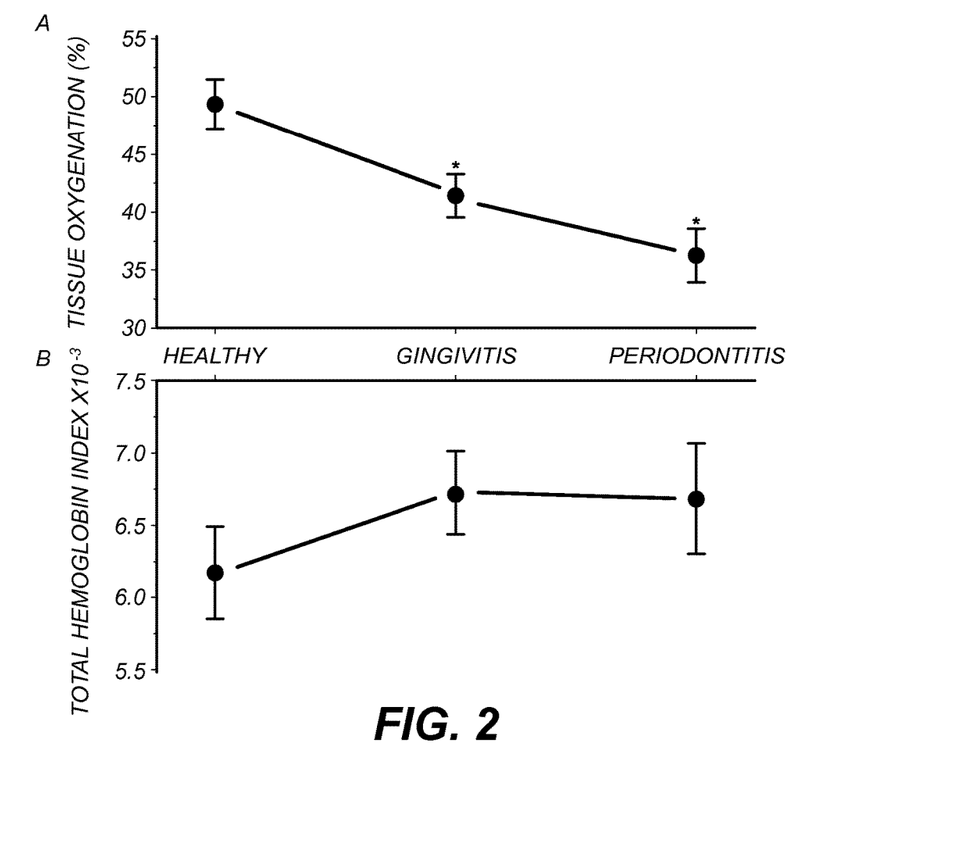
FIG. 2 is a diagram that illustrates tissue oxygenation decreases at sites with gingivitis and periodontitis relative to healthy tissue and that the total hemoglobin index increases at sites with gingivitis and periodontitis relative to healthy tissue.

Another study has indicated the same trends, except that the concentration of tHb is more sensitive to the change from health to gingivitis, less sensitive to the progress from gingivitis to periodontitis. FIG. 2 is a diagram that illustrates tissue oxygenation decreases at sites with gingivitis and periodontitis relative to healthy tissue and that the total hemoglobin index increases at sites with gingivitis and periodontitis relative to healthy tissue. The oxygenation level change has almost the same sensitivity to both disease stages.

Figure 3:
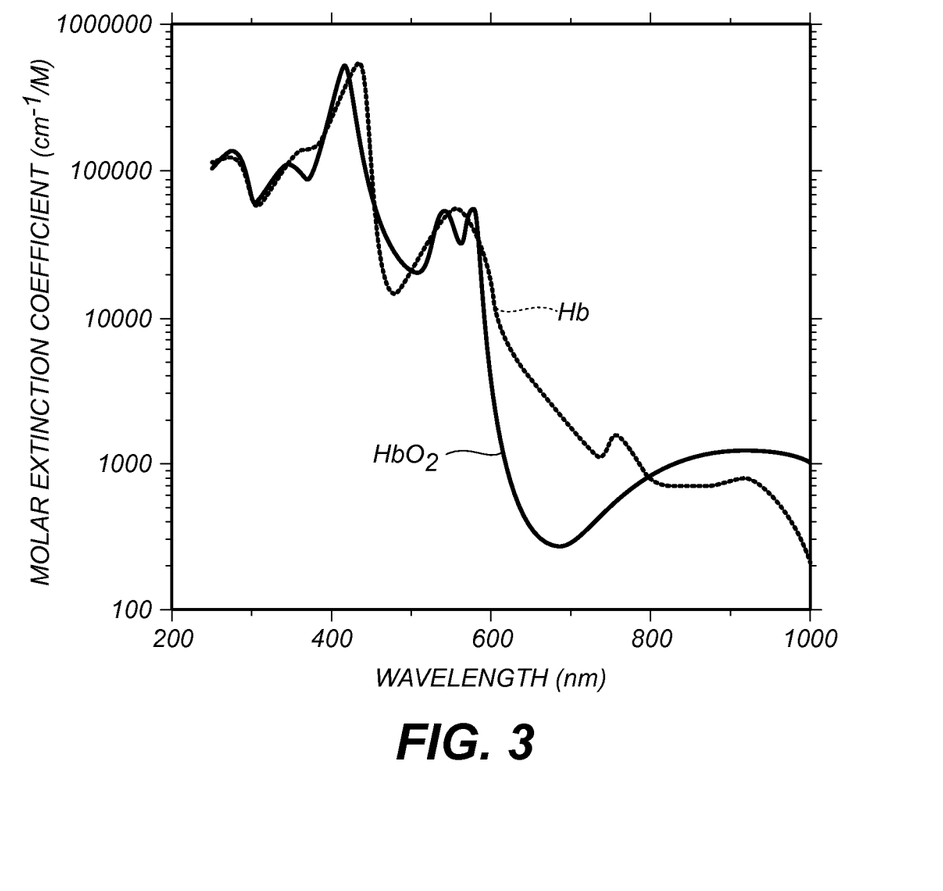
FIG. 3 is a diagram that illustrates molar extinction coefficients of oxy-hemoglobin ($HbO_2$) and deoxy-hemoglobin (Hb) over a visible and near infrared range spectral range for soft tissues.

Since oxy- and deoxy-hemoglobin are the main absorbing compounds of soft tissues in visible and near infrared range, the characteristics of light attenuation in tissues is determined mainly by the extinction coefficients of hemoglobin over this spectral range. FIG. 3 is a diagram that illustrates oxy-hemoglobin's ($HbO_2$) and deoxy-hemoglobin's (Hb) molar extinction coefficients over a visible and near infrared range spectral range for soft tissues. The diffuse reflectance spectra of tissues can be used to calculate the relative concentration of tHb and its oxygenation level.

Figure 4:
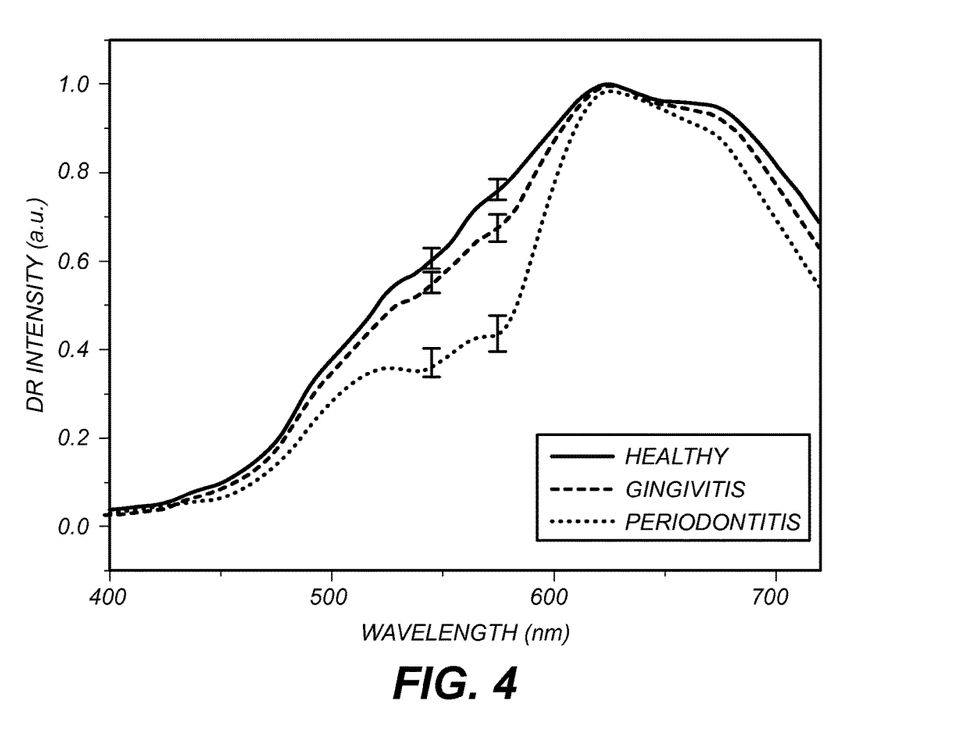
FIG. 4 is a diagram that illustrates a diffuse reflectance (DR) intensity over a visible spectral range for healthy tissue, gingivitis tissue, and periodontitis tissue.

Some studies have shown that diffuse reflectance spectroscopy of periodontal tissues can be used to calculate the relative concentration of hemoglobin and its oxygenation level. One study recognized that spectroscopic information of periodontal tissue are obtainable to a good extend through diffuse reflectance images of the gum captured at various illumination wavelengths. FIG. 4 is a diagram that illustrates a diffuse reflectance intensity over a visible spectral range for healthy tissue, gingivitis tissue, and periodontitis tissue. However, multispectral imaging setups used in such studies are large and were used to assess gum tissues on the buccal surface in the frontal teeth; but could not be used on the lingual surface or posterior teeth. As such, Applicants note that their utility is limited to scientific studies and not suitable for general clinical use.

To obtain in vivo images of periodontal tissues, Applicants employ a multispectral imaging technique to measure light attenuation in tissues. The multispectral imaging technique is related to the spectroscopic technique. Based on the multispectral imaging technique, exemplary imaging based systems and/or method embodiments can be developed to quantify the relative concentration of $HbO_2$ and Hb and its oxygenation level, thereby determining periodontal tissue conditions.

The diffuse reflectance intensity of tissues, R, at one wavelength is determined by the concentrations of $HbO_2$ and Hb in tissues and their effective attenuation coefficients, A1 and A2, at that wavelength:

$$\ln(R) = -(A1*[HbO_2] + A2*[Hb]) + \ln(k), \quad (1)$$

where ln(k) is a constant term which can be removed by calibration.

Total hemoglobin concentration, tHb, and oxygen saturation, $S_tO_2$, are defined as:

$$tHb = [HbO_2] + [Hb] \quad (2)$$

$$S_tO_2 = [HbO_2]/tHb \quad (3)$$

Theoretically, the diffuse reflectance intensities at any two wavelengths can be used to calculate the concentrations of $HbO_2$ and Hb, so that the total concentration of hemoglobin and its oxygenation level can be calculated. The periodontal tissue conditions can then be assessed based on these quantities.

Since the extinction coefficients of $HbO_2$ and Hb change over the spectral range (see FIG. 3), wavelength selection in measuring light attenuation is desirable.

Although the reflectance intensities at any two wavelengths might be used, particular wavelength selections can provide more accurate and reliable measurement.

Referring to FIGS. 3 and 4, Applicants have recognized that the following three wavelengths are good candidates:
- 575 nm: Oxy- and deoxy-hemoglobin have strong absorption at 575 nm. At this wavelength, reflectance intensity is more sensitive to change in total hemoglobin concentration in tissues than at other wavelengths in the visible-NIR range.
- 610 nm to 630 nm: The absorption coefficient of Hb is 7 to 8 times of the absorption coefficient of $HbO_2$ in this wavelength range, so that reflectance intensity mainly reflects change in Hb concentration. Also, the peak of the spectral reflectance curve occurs in this range.
- 800 nm: The absorption coefficients, and thus the effective attenuation coefficients of $HbO_2$ and Hb are approximately equal (or isobestic) at this wavelength. For example, the reflectance intensity for a narrow wavelength band including 800 nm can be a good measure of the relative total concentration of hemoglobin. In one embodiment, the comparison of reflectance intensity changes between 800 nm and 610 nm~630 nm can indicate the oxygenation level changes in the soft tissue (e.g., in the gums or mouth).

According to the absorption characteristics of hemoglobin in periodontal tissue in its various health conditions, the spectral reflectance intensities are changed in predictable ways. By monitoring the tissue's reflectance at various wavelengths, information can be derived to help determine periodontal health.

The present application describes methods and apparatus embodiments for assessing gingival health by making use of reflectance intensity values obtained from multi-spectral images.

In a preferred exemplary embodiment, Applicants can employ the reflectance intensity ratio at 575 nm and 620 nm, 1575/1620, or the reflectance intensity ratio at 575 nm and 800 nm, 1575/1800, to determine the relative concentration of total hemoglobin in tissues; and employ the reflectance intensity ratio at 620 nm and 800 nm, 1620/1800, to determine the oxygenation level of tissues. This information can provide suitable information to aid in the detection of periodontal disease.

Some have attempted to use the reflectance intensity ratios at 615 nm and 460 nm, at 620 nm and 575 nm, and at 629 nm and 545 nm to detect periodontal inflammation. Detection criteria were drawn from a single reflectance intensity ratio, monitoring Hb and $HbO_2$ concentration. As noted by Ge et. al. (Z. Ge, K. Z. Liu, X. Xiang, ect. "Assessment of Local Hemodynamics in Periodontal Inflammation Using Optical Spectroscopy"), difference in the total hemoglobin index may be modest between healthy and inflamed gum, and nonexistent between gingivitis and periodontitis. Therefore, sensitivity and accuracy of methods that only monitor Hb and $HbO_2$ concentration can be limited.

Exemplary embodiments of the present application can employ at least two reflectance intensity ratios, such as 1575/1620 and 1620/1800 (or 1575/1800 and 1620/1800), to obtain information about both total hemoglobin concentration and oxygenation saturation level of tissues, respectively. By detecting changes in both total hemoglobin concentration and oxygenation saturation level simultaneously, the present application promotes sensitivity and accuracy in assessing periodontal disease conditions.

In one exemplary embodiment, instead of taking ratios of spectral reflectance values, Applicants have recognized that reflectance intensities at different wavelengths, as obtained from multispectral images, can be used with Equation (1) to directly determine the concentration of Hb and $HbO_2$.

As an alternate embodiment, the set of reflectance intensities Ri, measured from the $i^{th}$ image of a set of images captured at n wavelengths, generate the following set of linear equations:

$$\ln(R1) = A11*[HbO_2] + A21*[Hb]; \quad (4)$$

$$\ln(R2) = A12*[HbO_2] + A22*[Hb]; \quad (5)$$

$$\ln(Rn) = A1n[HbO_2] + A2n*[Hb]; \quad (6)$$

Values of effective attenuation coefficients A1i and A2i are generally known for the visible wavelength. [$HbO_2$] and [Hb] can be determined from two (e.g., n=2) diffuse reflectance images captured at two different wavelengths. This embodiment may require an imaging device with very high performance and signal-to-noise ratio.

Alternatively, with images captured at more than two (n>2) wavelengths, the set of Equation (4) becomes an over-determined system, and an optimized solution for [$HbO_2$] and [Hb] can be determined from curve fitting, without putting a high requirement on the performance of the imaging device.

Once [$HbO_2$] and [Hb] are determined, the hemoglobin concentration and oxygenation level can be calculated from Equations (2) and (3).

Some known multispectral imaging setups are large. They were used to assess gum tissues on the buccal surface in the frontal teeth; they could not be used on the lingual surface or posterior teeth. As such, Applicants note that their utility is limited to scientific studies and not suitable for general clinical use.

The present application describes exemplary intraoral multispectral imaging apparatus embodiments for periodontal assessment that can be small and readily usable on gum tissues on all surfaces and all teeth inside the mouth cavity, and methods for using the same.

Figure 5:
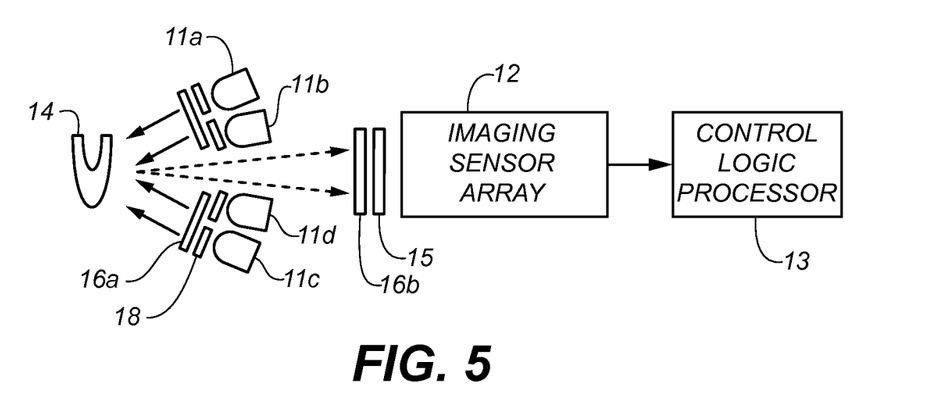
FIGS. 5 and 6 are diagrams that respectively illustrate an exemplary multispectral imaging apparatus embodiment that can be packaged into an exemplary handheld multispectral intraoral camera embodiment according to the application.
Figure 6:
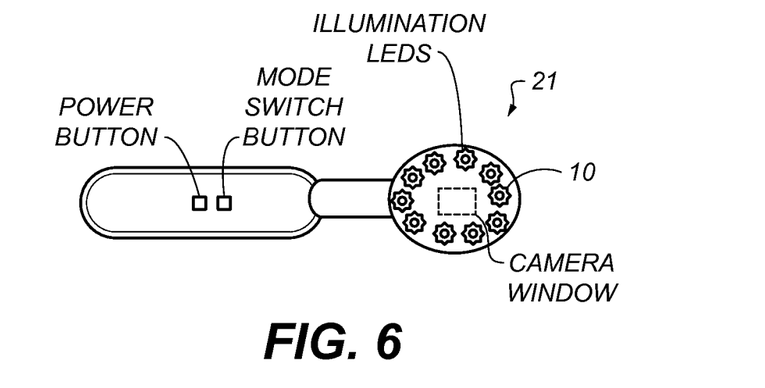

FIGS. 5 and 6 are diagrams that respectively illustrate an exemplary multispectral imaging apparatus embodiment that can be packaged into an exemplary handheld multispectral intraoral camera embodiment according to the application. As shown in FIG. 5, there is illustrated an exemplary multispectral imaging apparatus 20 of the present application. As shown in FIG. 6, the apparatus 20 can be packaged into a handheld multispectral intraoral camera 21.

An illumination module 10 can include one or multiple light sources 11 that provide illumination light. Four light sources 11 (illustrated as 11a, 11b, 11c, and 11d) are shown by way of example, though there can be any number of different wavelengths and more than a single light source for each wavelength.

An imaging sensor array 12, which may be color or monochrome and may be a charge-coupled device, complementary metal-oxide semiconductor imaging array or the like, can provide a set of output values for each pixel corresponding to light from light sources 11 reflected back from gum tissue 14 and imaged by imaging optics (not shown). Imaging sensor array 12 can be connected to a display 17 (not shown) external to the apparatus for image display. Light sources 11 and imaging sensor array 12 are both connected to a control logic processor 13. Timing for illumination by light sources 11 and image capture by imaging sensor array 12 is controlled by control logic processor 13. Control logic processor 13 can be an embedded microprocessor chip, or it can be the central processing unit of a computer that the multispectral imaging apparatus 20 connects to, or the like.

Optionally, a polarizer 16a may be disposed at the output of light sources 11, and another polarizer 16b oriented 90° with respect to polarizer 16a is placed between gum tissue 14 and image sensor array 12. Polarizer 16a provides linearly polarized light for illuminating gum tissue 14. Inclusion of polarizer 16b would provide to image sensor array 12 only light that is orthogonally polarized with respect to illumination light. This arrangement can minimizes or reduce specular reflection in the image signal.

In one exemplary embodiment, light sources 11 are narrowband light sources (11a, 11b, 11c, and 11d) having wavelength bands λ1, λ2, λ3, and λ4, respectively, providing spectrally discriminating illumination. Narrowband light sources 11a, 11b, 11c, and 11d can be different color LEDs, lasers, or the like, or polychromatic light (or more simply called white light) sources with narrow bandpass filters 18 at different center wavelengths. Even if LEDs are used, bandpass filters 18 with passbands narrower than the spectra of the LEDs can be used to provide greater spectral discrimination.

In a further exemplary embodiment, light sources 11 are polychromatic light sources providing white light illumination. With white light illumination, a band-selectable spectral filter 15 can be positioned between gum tissue 14 and imaging sensor array 12 to provide the reflected light to imaging sensor array 12 in narrow spectral bands. The band-selectable spectral filter 15 can be a filter wheel with predetermined passbands or an electrically tunable filter, such as one composed of liquid crystal or acousto-optic modulator, or the like, and can be controlled by control logic processor 13.

Light reflected from gum tissue 14 is imaged by image sensor array 12 in narrow spectral bands, either originating from narrowband light sources or as a result of filtering by band-selectable spectral filter 15. To obtain different wavelength band reflectance images, narrowband light sources 11a, 11b, 11c, and 11d or band-selectable spectral filter 15 can be energized by control logic processor 13 according to color groups, one color group at a time in rapid succession, and the corresponding measurements of reflected light are obtained by imaging sensor array 12.

In accordance with at least one embodiment described, one spectral passband imaged by image sensor array 12 is centered at 575 nm; the other is centered at 620 nm or 800 nm. Reflectance image intensity ratio of the spectral bands at 575 nm and 620 nm or the spectral bands at 575 nm and 800 nm provide the information needed to determine the relative concentration of total hemoglobin in gum tissues.

In at least one exemplary embodiment, all three spectral passbands, centering at 575 nm, 620 nm, and 800 nm, are imaged by image sensor array 12; reflectance image intensity ratio of the spectral bands at 575 nm and 620 nm or the spectral bands at 575 nm and 800 nm, together with reflectance image intensity ratio of the spectral bands at 620 nm and 800 nm, provide the information needed to determine the relative concentration of total hemoglobin as well as oxygen saturation level in tissues.

Throughout this application, when center wavelength is specified, it is understood that the actual center wavelength needs not to be exactly as specified, but suffices to be in the neighborhood of the specified wavelength.

In another exemplary embodiment, at least three spectral passbands, centering at different wavelengths, are imaged by image sensor array 12. The at least three reflectance intensities provide the information needed to solve the system of Equations (4)-(6) using standard linear algebra techniques to determine $[HbO_2]$ and $[Hb]$, whereby the total hemoglobin concentration and oxygenation level can be calculated from Equations (2) and (3).

In one exemplary embodiment, calculation of the reflectance intensity ratios or the solving of the system of Equations (4)-(6) can be performed by control logic processor 13.

In one exemplary embodiment, multispectral intraoral camera 21 can include at least two modes of operation: video and still capture modes.

In video mode, illumination module 10 can provide illumination while a live preview image is shown on display 17. This live preview image allows the user to find the site/region of interest and position multispectral intraoral camera 21. To provide color preview image, polychromatic light sources 11, such as white LEDs, and a color imaging sensor array 12 are used. If a monochrome imaging sensor array 12 is used, narrowband light sources 11 comprised of red, green, and blue light, can be turned on in a rapid color sequence; the three respective monochrome images are combined to generate a color live preview.

In still capture mode, different wavelength band reflectance images are obtained (e.g., sequentially in the manner described above), with control logic processor controlling narrowband light sources 11a, 11b, 11c, and 11d or band-selectable spectral filter 15 in synchronization with image capture by imaging sensor array 12.

Once reflectance images are captured at selective wavelengths, the images are processed for determination and display (e.g., mapping) of periodontal health conditions.

In one exemplary embodiment, a color map can be used to illustrate/highlight the disease areas on the raw images after processing.

Processing can be done by control logic processor 13, by an external computer or the like, alone or in combination. In one processing algorithm, the captured reflectance images are used to calculate reflectance intensity ratios or the solving of the system of Equations (4)-(6) to determine the relative total concentration of hemoglobin tHb and its oxygenation level $S_tO_2$ for each pixel of the image. The results can be displayed as a color map image by assigning false colors to all of the image pixels according to calculated relative values of tHb, $S_tO_2$, or a combination of the two.

Pixels having a certain color, corresponding to certain range of values of tHb, $S_tO_2$, or the two combined in some manner, as predetermined through clinical verifications, indicates that the region has a high likelihood of having periodontal disease conditions (e.g., gingivitis tissue, or periodontitis tissue).

Figure 7A:
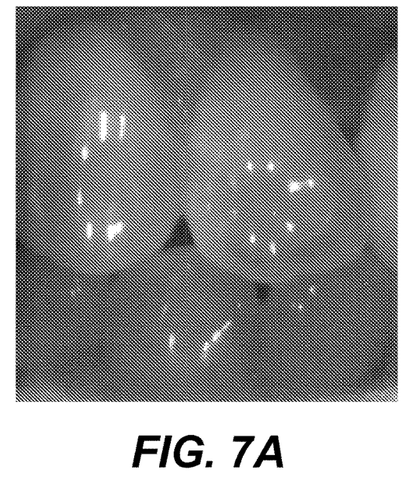
FIGS. 7A-7D are diagrams that illustrate an exemplary result of data representing soft tissue detected at more than two selected wavelengths and a generated result where a first color (e.g., texture, indication) represents healthy gum tissue while a second color or third color (e.g., texture, indication) represents inflamed gum tissue or conditions of periodontal disease.
Figure 7B:
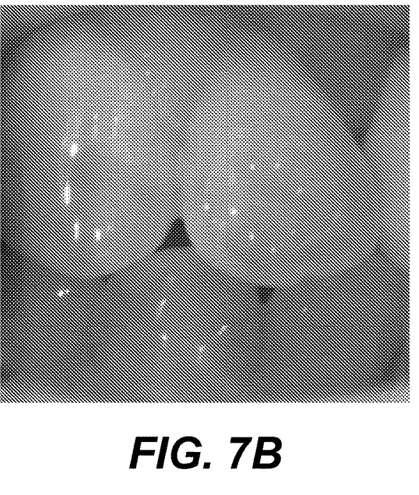
Figure 7C:
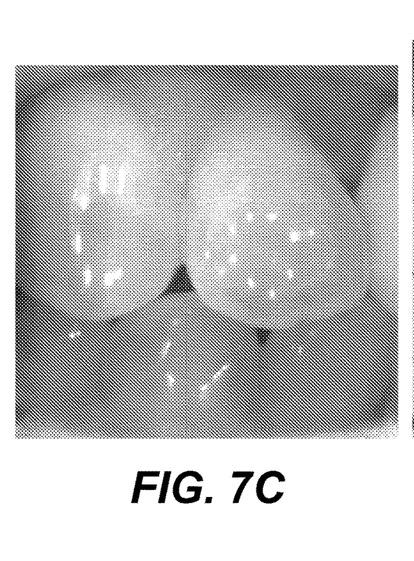
Figure 7D:
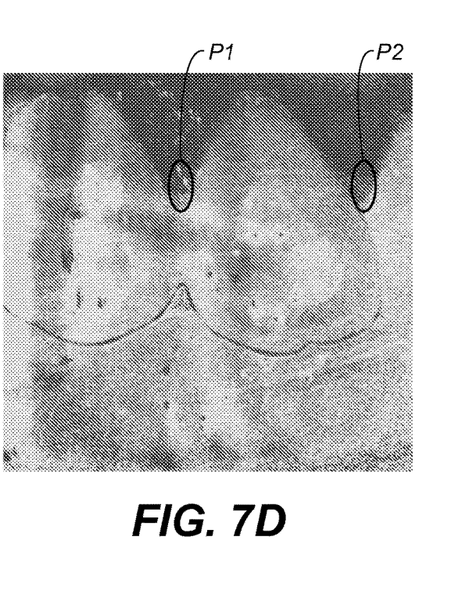

An example of such result is shown in FIGS. 7A-7D. FIGS. 7A, 7B, and 7C are the reflectance images captured at 575 nm, 620 nm and 800 nm, respectively. FIG. 7D is the generated color map where a first color (e.g., blue or a dark color) represents healthy gum tissue while a second color (e.g., magenta or a light color) represents inflamed gum tissue. As shown in FIG. 7D, the displayed color map shows one papilla site (P1) without inflammation, and the other site (P2) with light inflammation. Preferably, the displayed periodontal disease condition can be displayed on a segmented image of a patient mouth or region thereof, namely segmented into a soft tissue/gum region; or segmented into teeth, background and soft tissue regions. In one exemplary embodiment, a first texture fill can correspond to regions of slight inflammation and a second texture fill (e.g., within a segmented soft tissue region) can indicate regions of moderate or more severe tissue inflammation.

Figure 8A:
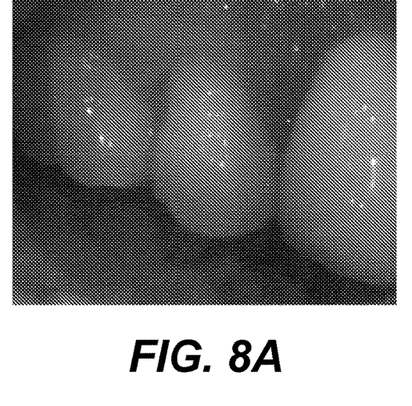
FIGS. 8A-8D are diagrams that illustrate an exemplary result of data representing soft tissue detected at more than two selected wavelengths and a generated result where a first color (e.g., texture, indication) represents healthy gum tissue while a second color or third color (e.g., texture, indication) represents inflamed gum tissue or conditions of periodontal disease.
Figure 8B:
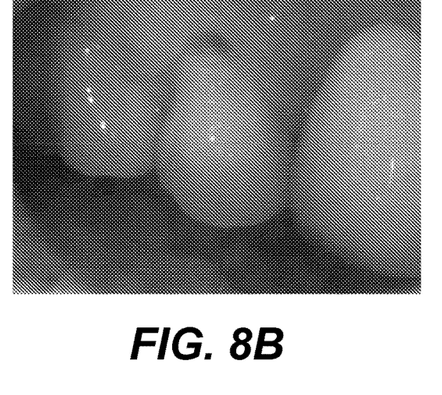
Figure 8C:
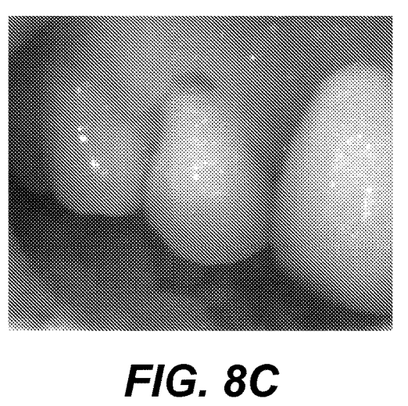
Figure 8D:
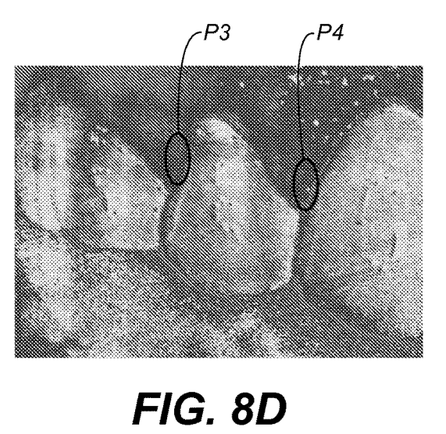

An example of such result is shown in FIGS. 8A-8D. FIGS. 8A, 8B, and 8C are the reflectance images captured at 575 nm, 620 nm and 800 nm, respectively. As shown in FIG. 8D, one site (P3) shows mild inflammation, and the other site (P4) shows severe inflammation.

Figure 9:
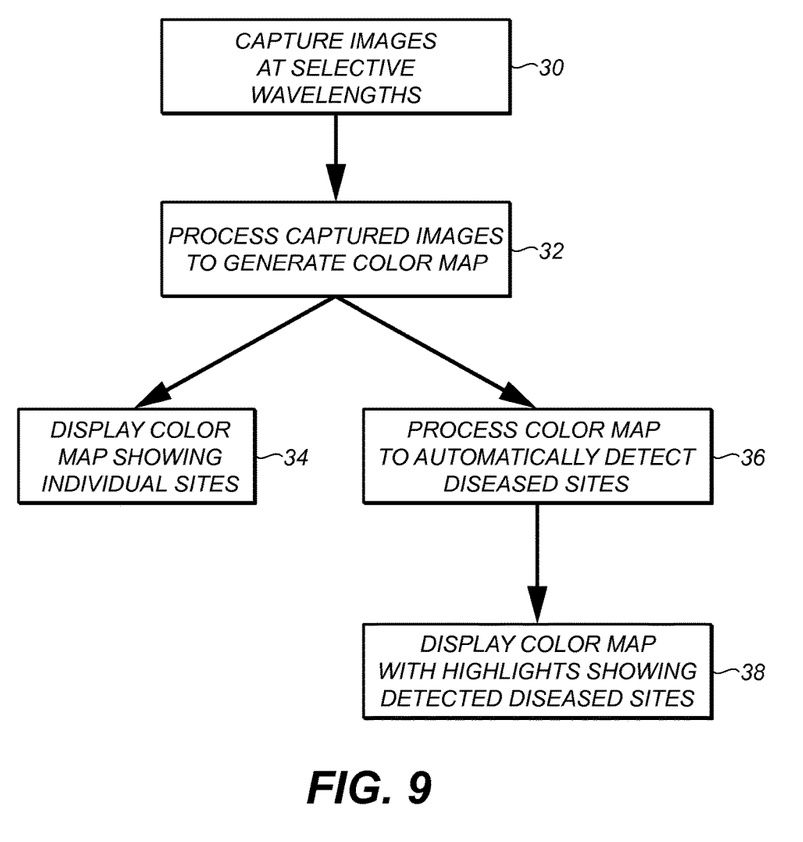
FIG. 9 shows an exemplary workflow of the multispectral intraoral camera according to embodiments of the present application as an aid to detect periodontal diseases.

FIG. 9 shows an exemplary workflow of an exemplary multispectral intraoral camera 21 of the present application as an aid to detect periodontal diseases. Referring to FIG. 9, a flow chart that shows an exemplary method of operating a multispectral intraoral camera according to embodiments of the application will now be described. As shown in FIG. 9, the method for operating an exemplary multispectral intraoral camera as an aid to detect periodontal diseases will be described using and can be implemented by embodiments of multispectral intraoral apparatus/camera shown in FIGS. 5-6; however, the method of FIG. 9 is not intended to be limited thereby.

As shown in FIG. 9, reflectance images of the gum tissue at selective wavelengths are captured (Step 30). Processing can be done by control logic processor 13, by an external computer or the like, alone or in combination. In one exemplary embodiment, the captured reflectance images can be image processed by control logic processor 13 or an external computer to calculate reflectance intensity ratios or to solve of the system of Equations (4)-(6) to determine the relative total concentration of hemoglobin tHb and its oxygenation level StO2 for at least a subset of pixels in the respective images. Exemplary results can be displayed (e.g., highlighted, listed) in correspondence to certain range of values of tHb, StO2, or the two combined in some manner, as predetermined through clinical verifications to indicate that such highlighted regions can have a high likelihood of periodontal disease conditions (e.g., gingivitis tissue, or periodontitis tissue). In one embodiment, captured images are then processed to generate color map (Step 32), as described above in FIG. 7D. In one embodiment, captured images are then processed to generate a digital periodontal chart of at least a portion of the mouth (Step 32), as described below in FIG. 10. The combined image or raw images of the soft tissue (e.g., color map) generated from each captured region can be displayed, showing the individual sites of interest (Step 34). Alternatively, the color map can be processed by control logic processor 13 to automatically detect diseased sites (Step 36). The detected diseased sites can be highlighted on the color map in the display (Step 38).

Figure 10:
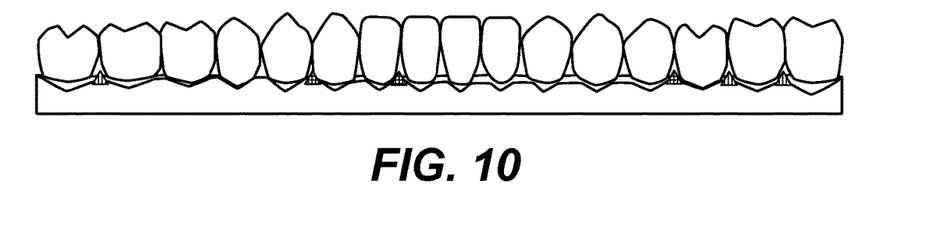
FIG. 10 is a diagram that illustrates automatically detected diseased sites (e.g., that can be labeled or highlighted in a digital periodontal chart of the whole mouth (or a portion thereof) according to embodiments of the present application.

In one exemplary embodiment, steps 36 and 38 are carried out for color maps of gum tissue of all teeth, the automatically detected diseased sites can be labeled or highlighted in a digital periodontal chart of the whole mouth, such as that shown in FIG. 10.

In one embodiment, each suspected area of interest (AOI) (e.g., diseased area) determined within a dental region of interest (ROI) (e.g., a portion of the teeth or jaw) by hemoglobin and its oxygenation characteristics can be configured to be accepted or rejected by additional operator action by a dental professional (e.g., visual inspection, testing and/or tactile probing) before an area of interest is determined to be a diseased site or displayed in a visual representation of the dental ROI. Alternatively, a visual representation of the AOI in the dental ROI can be displayed, stored, and/or transmitted.

In a typical periodontal examination session using the apparatus of this application, reflectance images are captured and color maps are generated for gum tissue of all teeth. In this case, control logic processor 14 can process all of the reflectance images, matching them together to form a stitched image of the whole dentition. The stitched image can be displayed with highlights on all the periodontal sites that have been automatically detected to have disease conditions, or it can be simply displayed as a stitched color map of the whole dentition.

Although certain exemplary embodiments herein disclosed detected diseased sites can be highlighted on a color map in a display (e.g., step 38), embodiments of the application are not intended to be so limited because any ways known to one of ordinary skill in the art can be used to highlight areas of interest or likely disease described herein (e.g., textures, words, mapping, video, etc.).

Applicants have described system and method embodiments wherein periodontal tissue conditions can be detected by the relative total concentration of hemoglobin and its relative oxygenation level.

Applicants have described system and method embodiments wherein relative concentration of tHb and its relative oxygenation level can be used to detect periodontal diseases.

Applicants have described system and method embodiments wherein relative concentration of tHb can be calculated through ratio of diffuse reflectance intensities at 575 nm and 620 nm, or ratio of diffuse reflectance intensities at 575 nm and 800 nm.

Applicants have described system and method embodiments wherein relative oxygenation level can be calculated through ratio of diffuse reflectance intensities at 620 nm and 800 nm.

Applicants have described system and method embodiments wherein relative concentration of tHb and its relative oxygenation level can be calculated through ratio of diffuse reflectance intensities at 575 nm and 620 nm and ratio of diffuse reflectance intensities at 620 nm and 800 nm.

Applicants have described system and method embodiments wherein relative concentration of tHb and its relative oxygenation level can be calculated through ratio of diffuse reflectance intensities at 575 nm and 800 nm and ratio of diffuse reflectance intensities at 620 nm and 800 nm.

Applicants have described system and method embodiments wherein concentration of tHb and its oxygenation can be calculated through diffuse reflectance intensities at at least three wavelengths. Applicants have described a system and method wherein accurate and reliable measurements can be achieved by wavelength selection.

Applicants have described system and method embodiments wherein accurate and reliable measurements can be achieved by multi-wavelength imaging and calculations.

Applicants have described system and method embodiments wherein an intra-oral camera with multi-spectral imaging function can be developed to detect periodontal diseases.

Applicants have described system and method embodiments wherein an intra-oral camera with video mode and image mode can be used to assess periodontal diseases on situ.

Consistent with exemplary embodiments of the present application, a computer program utilizes stored instructions that perform on image data that is accessed from an electronic memory. As can be appreciated by those skilled in the image processing arts, a computer program for operating the imaging system in an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In one embodiment, a method of capturing a digital dental image can include illuminating a dental region of interest (ROI) using light sources; capturing reflectance images by receiving light reflected from ROI in narrow wavelength bands; processing captured reflectance images to determine relative tHb; identifying disease areas having periodontal tissues condition; and displaying, storing, or transmitting the identified disease areas having periodontal tissues condition.

In one embodiment, an intraoral camera can include an illumination module comprising light sources; an imaging sensor array receiving light reflected from tissue in narrow wavelength bands to capture reflectance images; a control logic processor for processing captured reflectance images for determining relative tHb for identifying disease areas having periodontal tissues condition; and a display for displaying periodontal tissues or for displaying a color map of the identified disease areas having periodontal tissues condition.

The invention has been described in detail, and may have been described with particular reference to a suitable or presently preferred embodiment, but it will be understood that variations and modifications can be effected within the spirit and scope of the invention. For example, display 17 can be mounted at the camera 21. Further, the display 17 (and/or imaging apparatus 20 or camera 21 can be coupled to an external processor or workstation for additional review, processing and/or control of transmission, storage, manipulation or display of images described herein. The presently disclosed embodiments are therefore considered in all respects to be illustrative and not restrictive. The scope of the invention is indicated by the appended claims, and all changes that come within the meaning and range of equivalents thereof are intended to be embraced therein.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. A method of capturing a digital dental image, comprising:
   illuminating a dental region of interest (ROI) using light sources;
   capturing reflectance images by receiving light reflected from ROI in narrow wavelength bands;
   processing captured reflectance images to determine relative tHb concentration and its oxygenation level using at least a wavelength band that includes an isobestic wavelength for absorption coefficients of oxyhemoglobin (HbO2) and deoxyhemoglobin (Hb), wherein the processing includes generating reflectance intensity ratios, including an isobestic intensity from the captured reflectance images, in combination, to determine the relative tHb concentration and its oxygenation level;
   identifying selected areas of interest (AOI) within the dental ROI having selected pixel image characteristics of both hemoglobin's total concentration and oxygenation level; and
   displaying, storing, or transmitting the identified AOI within the dental RO.

2. The method of claim 1 where the illuminating includes at least one light emitting diode (LED) or a white light source and the capturing includes a monochromatic sensor or a color sensor.

3. The method of claim 1 where the processing includes solving a set of equations using the intensities of the captured reflectance images at at least three wavelengths.

4. An intraoral camera comprising:
   an illumination module comprising light sources;
   an imaging sensor array receiving light reflected from tissue in narrow wavelength bands to capture reflectance images, where the reflectance images are captured at at least three wavelengths, where one of the at least three wavelengths includes an isobestic wavelength for absorption coefficients of oxyhemoglobin (HbO2) and deoxyhemoglobin (Hb);
   a control logic processor for processing the captured reflectance images to determine relative tHb concentration and its relative oxygenation level for identifying disease areas having periodontal tissues condition, wherein the control logic processor generates reflectance intensity ratios, including an isobestic intensity from the captured reflectance images, in combination, to determine the relative tHb concentration and its relative oxygenation level; and
   a display for displaying periodontal tissues or for displaying a color map of the identified disease areas having periodontal tissues condition.

5. The intra-oral camera of claim 4, where the isobestic wavelength for absorption coefficients of oxyhemoglobin (HbO2) and deoxyhemoglobin (Hb) is near 800 nm.

6. The intra-oral camera of claim 4 wherein the illumination module includes at least one light emitting diode (LED), and the sensor is a monochromatic sensor, wherein the at least one light emitting diode (LED) illuminates at various wavelengths.

7. The intra-oral camera of claim 4 wherein the illumination module includes a plurality of light emitting diodes (LEDs) illuminating at various wavelengths, and the sensor is a monochromatic sensor.

8. The intra-oral camera of claim 4, where the reflectance intensity ratios are between intensities of reflectance images at 575 nm and 620, or between intensities of reflectance images at 575 nm and 800 nm.

9. The intra-oral camera of claim 4, where the control logic processor further determines relative oxygenation level of hemoglobin.

10. The intra-oral camera of claim 4, wherein the reflectance intensity ratios are between intensities of reflectance images at 575 nm and 800 nm, and between intensities of reflectance images at 620 nm and 800 nm.

11. The intra-oral camera of claim 4 wherein the color map is based on ranges of reflectance intensity ratios.

12. The intra-oral camera of claim 4, where the control logic processor solves a set of equations using the intensities of the captured reflectance images at the at least three wavelengths.

13. The intra-oral camera of claim 4 wherein the control logic processor processes the generated color map to automatically identify disease areas having periodontal tissues condition.

14. The intra-oral camera of claim 4, wherein the identified disease areas are labeled or highlighted in a periodontal chart image.

15. The intra-oral camera of claim 4 wherein the control logic processor processes multiple captured reflectance images to stitch them together.

16. The intra-oral camera of claim 15, where the stitched image is displayed as color maps or with highlights of identified disease areas having periodontal tissues condition.

* * * * *